US006432934B1

(12) United States Patent
Gilbard

(10) Patent No.: US 6,432,934 B1
(45) Date of Patent: Aug. 13, 2002

(54) METHODS AND COMPOSITIONS FOR TOPICAL TREATMENT OF EYE SURFACE INFLAMMATION AND RELATED DRY EYE DISEASE

(75) Inventor: Jeffrey P. Gilbard, Weston, MA (US)

(73) Assignee: Advanced Vision Research, Woburn, MA (US)

(*) Notice: Subject to any disclaimer, the term of this patent is extended or adjusted under 35 U.S.C. 154(b) by 0 days.

(21) Appl. No.: 09/130,638

(22) Filed: Aug. 6, 1998

(51) Int. Cl.⁷ .............................................. A61K 31/65
(52) U.S. Cl. ...................................... 514/152; 514/912
(58) Field of Search ................................. 514/152, 912

(56) References Cited

U.S. PATENT DOCUMENTS

| | | | | |
|---|---|---|---|---|
| 4,772,460 A | * | 9/1988 | Malook et al. ................ | 424/10 |
| 4,911,933 A | | 3/1990 | Gilbard ........................ | 424/663 |
| 5,308,624 A | * | 5/1994 | Maincent et al. ............ | 424/427 |
| 5,789,395 A | * | 8/1998 | Amin et al. .................. | 514/152 |

FOREIGN PATENT DOCUMENTS

| | | |
|---|---|---|
| EP | 205 279 | 12/1986 |
| JP | 62 240629 | 10/1987 |
| WO | WO 99/58131 | 11/1999 |

OTHER PUBLICATIONS

Medline Abstract 76133934—Massey et al., 1976.*
Huber–Spitzy, V. et al., "Treatment of ocular chlamydial infection: Comparison of tetracyclines and norfloxacin," *Ophthalmologica*, 205(2):64–68 (1992).
Salamon, S.M. "Tetracyclines in ophthalmology," *Survey of Ophthalmology* 29(4):265–75 (1985).
Scott, C.A. et al., "Optometric clinical practice guideline care of the patient with ocular surface disease," *Ocular Surface Disease*, pp. 1–33 (1999), http://www.aoanet.org/cpg–10–cposd.html.
Van Gogh, E.R. et al., "Topical antibiotics in ophthalmology," *Pharmaceutisch Weekblad*, 129:156–163 (1994).
Bartholomew, R.S. et al. "Oxytetracycline in the Treatment of Ocular Rosacea: a Double–blind Trial" *British Journal of Ophthalmology* 66:386–388 (1982).
Belsheim, J. et al. "Tetracyclines and Host Defense Mechanisms: Interference with Leukocyte Chemotaxis" *Scand. J. Infect. Dis.* 11:141–145 (1979).
Bowman, R.W. et al. "Diagnosis and Treatment of Chronic Blepharitis" vol. VII Module 10, *Focal Points 1989: Clinical Modules for Ophthalmologists* American Academy of Ophthalmology, San Francisco (1989).
Brown, S.I. and Shahinian, L. Jr. "Biagnosis and Treatment of Ocular Rosacea" *Ophthalmol.* 85:779–786 (1978).
Dilly, P.N. and Mackie, I.A. "Distribution of Tetracycline in the Conjunctiva of Patients on Long Term Systemic Doses" *British Journal of Ophthalmology* 69:25–28 (1985).

Elewski, B.E. et al. "In Vivo Suppression of Neutrophil Chemotaxis by Ststemically and Topically Administered Tetracycline" *Journal of the American Academy of Dermatology* 8(6):807–812 (1983).
Esterly, N.B. et al. "Neutrophil Chemotaxis in patients With Acne Receiving Oral Tetracycline Therapy" *Arch. Dermatol.* 120:1308–1313 (1984).
Forsgren, A. et al. "Effect of Tetracycline on the Phagocytic Function of Human Leukocytes" *The Journal of Infectious Diseases* 130(4):412–415 (1974).
Friend, J. et al. "Glycogen and DNA Content of Corneal Epithelium: Comparison of Preparation Methods" *Invest. Ophthalmol. Vis. Sci.* 24:203–207 (1983).
Gilbard, J.P. and Rossi, S.R. "An Electrolyte–based Solution that Increases Corneal Glycogen and Conjunctival Goblet-cell Density in a Rabbit Model for *Keratoconjunctivitis sicca*" *Ophthalmology* 99:600–604 (1992).
Gilbard, J.P. et al. "A New Rabbit Model For *Keratoconjunctivitis sicca*" *Invest. Ophthalmol. Vis. Sci.* 28:225–228 (1987).
Gilbard, J.P. et al. "Ophthalmic Solutions, the Ocular Surface, and a Unique Therapeutic Artificial Tear Formation" *American Journal of Ophthalmology* 107:348–355 (1989).
Gilbard, J.P. et al. "Tear Film and Ocular Surface Changes after Closure of the Meibomian Gland Orifices in the Rabbit" *Ophthalmology* 96:1180–1186 (1989).
Gilbard, J.P. et al. "Tear Film Osmolarity and Ocular Surface Disease in Two Rabbit Models For *Keratoconjunctivitis sicca*" *Invest. Ophthalmol. Vis. Sci.* 29:374–378 (1988).
Golub, L.M. et al. "Further Evidence that Tetracyclines Inhibit Collagenase Activity in Human Crevicular Fluid and From Outer Mammalian Sources" *Journal of Periodontal Research* 20:12–23 (1985).
Golub, L.M. et al. "Minocyline Reduces Gingival Collagenolytic Activity During Diabetes" *Journal of Periodonatal Research* 18:516–526 (1983).
Golub, L.M. et al. "Tetracyclines Inhibit Tissue Collagenase Activity" *Journal of Periodontal Research* 19:651–655 (1984).
Gutgesell, V.J. et al. "Histopathology of Meibomian gland Dysfunction" *American Journal of Ophthalmology* 94:383–387 (1982).
Hoeprich, P.D. and Warshauer, D.M. "Entry of Four Tetracyclines into Saliva and Tears" *Antimicrobial Agents and Chemotherapy* 5(3):330–356 (1974).

(List continued on next page.)

Primary Examiner—Zohreh Fay
(74) Attorney, Agent, or Firm—Lahive & Cockfield, LLP; Jane E. Remillard, Esquire; Ralph A. Loren, Esquire

(57) ABSTRACT

Ophthalmic compositions and methods of using the same to simultaneously treat eye surface inflammation and dry eye are disclosed. The ophthalmic preparation contains a tetracycline compound in aqueous solution. The preparation preferably further includes a balance of electrolytes sufficient to maintain or restore essentially normal levels of conjunctival mucus-containing goblet cells and corneal glycogen. These electrolytes can include potassium, chloride, bicarbonate, sodium, calcium, magnesium and phosphate.

17 Claims, 5 Drawing Sheets

OTHER PUBLICATIONS

Jenkins, M.S. et al. "Ocular Rosacea" *American Journal of Ophthalmology* 88:618–622 (1979).

Marks, R. and Harcourt–Webster, J.N. "Histopathology of Rosacea" *Arch. Derm.* 100:683–691 (1969).

Martin, R.R. et al. "Effects of Tetracycline on Leukotaxis" *The Journal of Infectious Diseases* 129(2):110–116 (1974).

Mathers, W.D. "Ocular Evaporation in Meibomian Gland Dysfunction and Dry Eye" *Ophthalmology* 100:347–351 (1993).

McCulley, J.P. and Dougherty, J.M. "Blepharitis Associated with Acne Rosacea and Seborrheic Dermatitis" *Int. Ophthalmol. Clin.* 25(1):159–172 (1985).

McCulley, J.P. "Blepharoconjunctivitis" *Int. Ophthalmol Clin.* 24(2):65–77 (1984).

Nicolaides, N. et al. "Meibum Lipids in Rosacea Blepharitis, and Chalazia" *Invest. Ophthalmol. Vis. Sci.* 24 (Suppl.):78 (1983).

Robin, J.B. et al. "In Vivo Transillumination Biomicroscopy and Photography of Meibomian Gland Dysfunction" *Ophthalmology* 92:1423–1426 (1985).

Salamon, S.M. "Tetracyclines in Ophthalmology" *Survey of Ophthalmology* 29(4):265–275 (1985).

Seedor, J.A. et al. "Systemic Tetracycline Treatment of Alkali–Induced Corneal Ulceration in Rabbits" *Arch. Ophthalmol.* 105:268–271 (1987).

Sherwood, M.B. et al. "Long–term Morphologic Effects of Antiglaucoma Drugs on the Conjunctiva and Tenon's Capsule in Glaucomatous Patients" *Ophthalmology* 96:327–335 (1989).

\* cited by examiner

METHODS AND COMPOSITIONS FOR TOPICAL TREATMENT OF EYE SURFACE INFLAMMATION AND RELATED DRY EYE DISEASE

GOVERNMENT FUNDING

This invention was made with government support under grant EY03373 from the National Eye Institute. The United States government has certain rights in the invention.

BACKGROUND OF THE INVENTION

This invention relates to therapeutic ophthalmic preparations and methods of using the preparations locally to treat eye surface inflammation including meibomianitis and related dry eye disease. More particularly, it relates to topical ophthalmic solutions containing tetracycline compounds to suppress eye surface inflammation, including meibomianitis, while maintaining or restoring conjunctival mucus-containing goblet cells.

Systemic tetracyclines are currently used to treat ocular rosacea, a condition characterized by eye surface inflammation, and a variety of related eye disorders such as blepharitis, meibomianitis, keratitits, conjunctival hyperemia, and eyelid hyperemia. Open-label prospective studies have been published describing a decrease in blepharitis and conjunctival hyperemia associated with ocular rosacea following systemic administration of tetracycline (1, 2). Systemic oxytetracycline treatment of ocular rosacea has also been tested in a double-masked trial and found to be more effective than placebo in inducing remissions (3). In the trial, it was reported that eyelid and conjunctival hyperemia responded well, as did the associated blepharitis.

Based on these studies and clinical experience, oral tetracyclines has been recommended for treating meibomianitis, blepharitis and eye surface inflammation (4, 5, 6). Meibomianitis is a disorder characterized by inflammation centered about the meibomian glands. When inflammation includes most of the eye lid, the general term "blepharitis" may be applied. When inflammation includes the conjunctiva, the term "conjunctivitis" applies. When inflammation involves the cornea, the term "keratitis" applies. The eye surface includes the eye lids, cornea and conjunctiva. Recently, it was observed that meibomianitis and eye surface inflammation develops in a rabbit model for meibomian gland dysfunction (7). Analogous findings have been reported in humans (8, 9). These studies show that meibomianitis leads to meibomian gland dysfunction, with loss of meibomian gland oil from the tear film, an increase in tear film evaporation, a loss of water from the tear film and the development of dry eye surface disease.

Specifically, in the aforementioned rabbit model of meibomian gland dysfunction, meibomian gland orifice closure increases tear film osmolarity and decreases corneal epithelial glycogen and conjunctival goblet-cell density. These decreases are analogous to those seen with keratoconjunctivitis sicca (commonly known as "dry eye") from lacrimal gland disease (10, 11). The clinical relevance of these data has been further supported by studies demonstrating that patients with meibomian gland drop out have significantly elevated tear film evaporative rates and tear film osmolarity (12).

Just how tetracyclines work in the treatment of ocular surface inflammatory disorders, such as ocular rosacea, meibomianitis, blepharitis, conjunctivitis and keratitis has previously been unknown. However, elsewhere in the body it has been known that tetracyclines have potent antibacterial properties, inhibit collagenase activity (15, 16, 17), and decrease leukocyte chemotaxis (18, 19, 20, 21) and phagocytosis (22). When administered systemically, tetracycline enters into the tears (13) and concentrates in goblet cells, around blood vessels, and on the external surface of the conjunctival epithelium (14). Systemic administration of tetracycline, however, has several drawbacks. For example, it often results in adverse side effects, including gastrointestinal irritation, vaginal yeast infection, sunlight sensitivity and systemic allergic reactions.

Accordingly, it is an object of this invention to provide an improved ophthalmic preparation for locally delivering a tetracycline compound to ocular surfaces. It is another object of this invention to provide an ophthalmic solution for locally delivering a tetracycline compound to ocular surfaces, while maintaining or restoring essentially normal levels of conjunctival mucus-containing goblet cells. It is a further object of this invention to provide an electrolyte-based tetracycline formulation for simultaneously treating inflammatory eye diseases, such as meibomianitis, and associated blepharitis and dry eye disorders.

Additional objects of the invention will be apparent from the following description.

SUMMARY OF THE INVENTION

A therapeutic preparation for ophthalmic use has been developed that provides the advantage of drug delivery and treatment or prevention of dry eye disease. The preparation contains an anti-inflammatory agent, such as a tetracycline compound, in an electrolyte-based solution which can be applied topically to the eye, permitting the maintenance or restoration of essentially normal levels of conjunctival mucus-containing goblet cells and corneal glycogen. The ophthalmic preparation thus provides the advantages of local tetracycline delivery to ocular surfaces without a substantial decrease in mucus-containing goblet cells or corneal glycogen typically associated with the use of standard ophthalmic preparations. The ophthalmic preparation provides the further advantage of increasing low goblet cell density and corneal glycogen levels associated with the dry eye surface disease resulting from meibomian gland dysfunction. In contrast, standard ophthalmic preparations have been shown in studies described herein to exacerbate the loss of goblet cells and corneal glycogen.

In general, the ophthalmic preparation contains an aqueous solution of a tetracycline compound in an amount sufficient to treat an ocular disease characterized by eye surface inflammation with our without dryness. The preparation preferably also includes a balance of electrolytes found in natural tear fluid required for ocular surface maintenance, function and repair. In preferred embodiments, these electrolytes are present in amounts sufficient to maintain or restore essentially normal levels of conjunctival goblet cells and corneal glycogen, thereby maintaining mucus-mediated lubrication and the potential for normal healing. In a particularly preferred embodiment, the tetracycline compound is contained in Solution 15, described in U.S. Pat. No. 4,911,933, the contents of which are hereby incorporated by reference.

Principal electrolytes employed in the invention include, but are not limited to, sodium and chloride, in combination with lesser amounts of potassium and bicarbonate. Typically, these electrolytes are present in the following concentration ranges:

Potassium between about 22.0 to 43.0 millimoles per liter (mM/l), preferably between about 23.0 to 42.0 mM/l;

Bicarbonate between about 29.0 to 50.0 mM/l, preferably between about 31.0 to 48.0 mM/l;

Sodium between about 130.0 to 140.0 mM/l, preferably between about 131.0 to 139.0 mM/l; and Chloride between about 118.0 to 136.5 mM/l, preferably between about 124.0 to 136.0 mM/l.

Additional electrolytes which can be employed in the ophthalmic preparation, in combination with the above-listed electrolytes include, but are not limited to, calcium, magnesium and phosphate. Typically, these electrolytes are typically present in the following concentration ranges:

Magnesium between about 0.3 to 1.1 mM/l, preferably between about 0.5 to 0.6 mM/l, Calcium between about 0.5 to 2.0 mM/l, preferably between about 0.6 to 0.8 mM/l, and Phosphate between about 0.8 to 2.2 mM/l, preferably between about 1.8 to 2.0 mM/l.

The concentration of the tetracycline compound will vary depending on the nature and severity of the eye surface inflammation being treated and the specific tetracycline compound used. Generally, for tetracycline, the concentration in solution will range from about 0.125% to 2% when the solution is isotonic or attains isotonicity. Any suitable tetracycline compound (including tetracycline derivatives, analogs and salts thereof) known in the art can be used, such as those described in further detail below.

Ophthalmic preparations of the present invention can be used in methods of treating ocular disorders characterized by eye surface inflammation, such as meibomianitis or eye surface redness. Typically, the preparation is applied topically to the surface of the eye in an amount sufficient to treat the disorder. The ophthalmic preparation can also be used to simultaneously reduce eye surface inflammation and dryness, based on the presence of an active tetracycline compound in an aqueous solution containing the necessary balance of electrolytes for ocular surface maintenance, function and repair. The ophthalmic preparation can further maintain or restore conjunctival goblet cells and corneal glycogen which are typically depleted in dry eye disorders.

These and other embodiments of the invention will be apparent from the following detailed description and working examples.

DETAILED DESCRIPTION OF THE INVENTION

Figure 1:
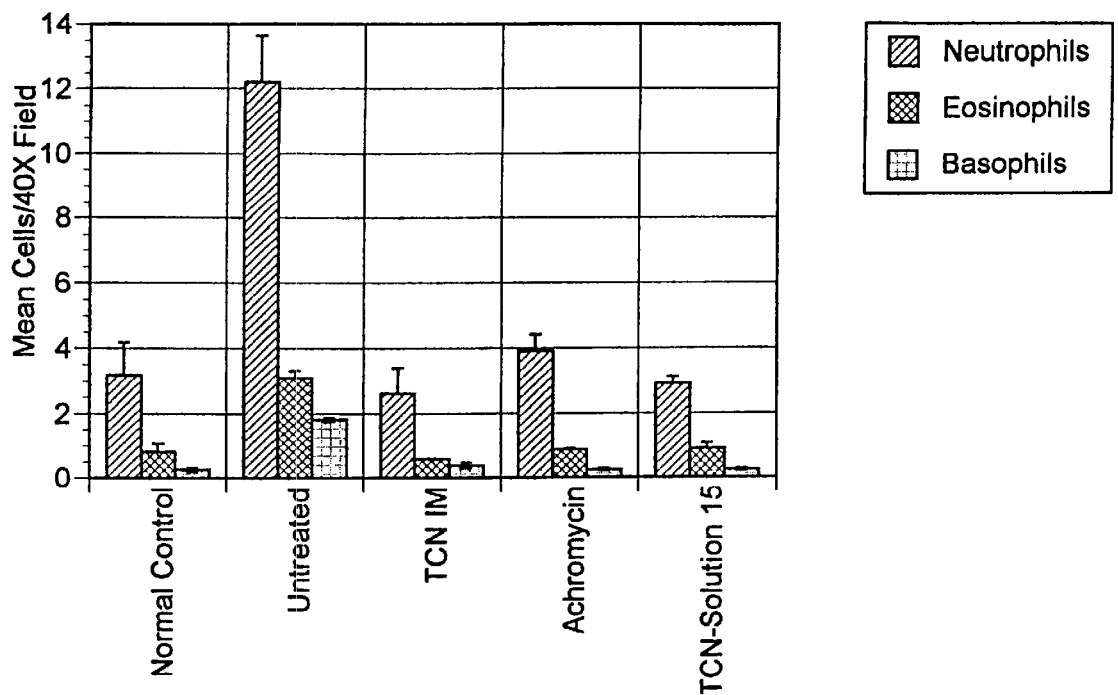
FIG. 1 is a graph showing leukocyte densities in tarsal conjunctival epithelium of (left to right) (a) normal control rabbits, (b) untreated control rabbits with meibomianitis/meibomian gland dysfunction, (c) rabbits treated with tetracycline in saline (administered intramuscularly (IM)), (d) rabbits treated with tetracycline in Achromycin™ light mineral oil eyedrops (administered topically), and (e) rabbits treated with tetracycline in Solution 15 (administered topically).

In accordance with the invention, a therapeutic ophthalmic preparation combines at least one tetracycline compound in an electrolyte-based aqueous solution to locally treat both eye surface inflammation and related dry eye disorders.

As used herein, the term "a tetracycline compound" refers to all known tetracyclines, tetracycline analogs, breakdown products, and derivatives thereof (e.g., HCL derivatives thereof). Such compounds are well known in the art, primarily for their potent anti-bacterial properties, and include, but are not limited to, methacycline, oxytetracycline, minocycline, demeclocycline, doxycycline, tetracycline, chlortetracycline, and salts thereof. These tetracycline compounds are described throughout the literature, for example, in the Merck Manual (e.g., Fifteenth Ed. (1987), p.38–39), the contents of which are incorporated by reference herein. It is preferable that the tetracycline is not highly photosensitive. In this respect, tetracycline and minocycline (as well as hydrochloride derivatives thereof) are preferred (Li et al. (1987) Biochem. Biophys. Res. Commun. 146:1191). From a functional standpoint, preferred tetracycline compounds for use in the invention are capable of inhibiting leukocyte chemotaxis. The aforementioned tetracycline compounds are commercially available, for example, from Sigma Chemical Corp., St. Louis, Mo.

In contrast to topical ointments and oil-based carriers known in the art, the tetracycline compound of the present invention is formulated in an aqueous solution, preferably containing electrolytes. Suitable concentrations of the tetracycline compound in solution include those equivalent in anti-inflammatory potency to tetracycline at a concentration range of between about 0.125% and 2% when the solution is isotonic or attains isotonicity.

The preparation preferably also includes a balance of electrolytes found in natural tear fluid required for ocular surface maintenance, function and repair. In preferred embodiments, these electrolytes are present in amounts sufficient to maintain or restore conjunctival goblet cells and corneal glycogen, thereby maintaining mucus-mediated lubrication and the potential for normal healing. This enables topical application of the preparation to ocular surfaces preferably without substantially reducing the density of conjunctival mucus-containing goblet cells or levels of corneal glycogen. Goblet cells form a critical layer of the tear film, providing the eye surface with lubrication, and playing an important role in the system that traps foreign matter that may enter the eye, and promptly removes it. Corneal glycogen is the energy source for the sliding step in corneal wound healing. Their preservation is therefore important in maintaining the health of ocular surfaces.

As used herein, the term "eye surface inflammation" includes any inflammatory disorder involving the ocular surface. The eye surface includes the eye lids, conjunctiva and cornea. Inflammation refers to white blood cell or leukocytic infiltration associated with cellular injury. Eye surface inflammatory disorders treatable by the ophthalmic preparation of the invention are typically manifested by signs and symptoms such as eye redness, or irritation. These diseases include, for example, meibomianitis, blepharitis conjunctival hyperemia, eyelid hyperemia, keratitis and ocular rosacea.

As used herein, the term "eye surface dryness" includes any ocular disorder resulting in loss of water from the tear film. Such disorders generally can be characterized by increased tear film osmolarity and decreased levels of corneal glycogen and conjunctival mucus-containing goblet cells. Eye surface dryness can result from a number of different diseases including, for example, meibomian gland dysfunction and meibomian gland orifice stenosis or closure.

As previously described herein, eye surface inflammatory disorders are often associated with eye surface dryness and irritation. Animal models for such combined ocular disorders have been produced, and can be used to test the efficacy of the ophthalmic preparations provided herein. For example, a rabbit model for meibomianitis and meibomian gland dysfunction has been developed (7). In this animal model, meibomian gland orifice closure results in the development of inflammation around the meibomian glands (i.e., meibomianitis), inflammation in the eyelids (blepharitis), inflammation in the conjunctiva (conjunctivitis) and in an increase in tear film osmolarity and a decrease in the levels of corneal glycogen and conjunctival mucus-containing goblet cells. As demonstrated in the Examples below, ophthalmic preparations of the invention effectively treat both the eye surface inflammation (i.e., meibomianitis) and associated eye surface dryness (elevated tear film osmolarity, decreased goblet cell density and reduced corneal glycogen) exhibited by this animal model. It is recognized that results of tests using rabbits has close correlation with humans and, therefore, that the results carry over to humans.

Ophthalmic preparations of the invention include aqueous solutions containing one or more tetracycline compounds which are, collectively, present in an amount sufficient to treat eye surface inflammation, such as meibomianitis or eye surface redness.

In preferred embodiments, ophthalmic preparations of the invention include, in addition to one or more tetracyclines, a balance of electrolytes naturally found in tear fluid. These electrolytes principally include major amounts of sodium and chloride, and lesser amounts of potassium and bicarbonate. The preparation may also contain other naturally-occurring elements of the tear fluid, such as proteins, enzymes, lipids and metabolites as described in U.S. Pat. No. 4,911,933. Typically, the potassium is present at a concentration of about 22.0 to 43.0 mM/l, the bicarbonate is present at a concentration of about 29.0 to 50.0 mM/l, the sodium is present at a concentration of about 130.0 to 140.0 mM/l, and the chloride is present at a concentration of about 118.0 to 136.5 mM/l. The osmolarity of the resulting solution is preferably in the range of about 296 to 325 mOsm/Kg, but water may be added or removed from the preparation to create appropriate therapeutic dilutions or concentrations.

The ophthalmic preparation can further optionally include calcium, magnesium and phosphate. In such embodiments, the calcium is preferably present at a concentration of about 0.5 to 2.0 mM/l, the magnesium is preferably present at a concentration of about 0.3 to 1.1 mM/l, and the phosphate is preferably present at a concentration of about 0.8 to 2.2 mM/l.

Accordingly, in a particular embodiment, the invention provides an ophthalmic solution having an osmolarity of about 296–325 mOsm/Kg, which includes at least the following components: (a) tetracycline at a concentration of about 0.125% to 2%; (b) potassium at a concentration of about 22.0 to 43.0 mM/l; (c) bicarbonate at a concentration of about 29.0 to 50.0 mM/l; (d) sodium at a concentration of about 130.0 to 140.0 mM/l, (e) chloride at a concentration of about 118.0 to 136.5 mM/l, (f) calcium at a concentration of about 0.5 to 2.0 mM/l, (g) magnesium at a concentration of about 0.3 to 1.1 mM/l, and (e) phosphate at a concentration of about 0.8 to 2.2 mM/l. Preferred concentrations of these components range from 0.25% to 1.50% for tetracycline, 23.0 to 42.0 mM/l potassium, 31.0 to 48.0 mM/l bicarbonate, 131.0 to 139.0 mM/l sodium, 124.0 to 136.0 mM/l chloride, 0.6 to 0.8 mM/l calcium, 0.5 to 0.6 mM/l magnesium, and 1.0 to 2.0 mM/l phosphate.

In a particularly preferred embodiment, the ophthalmic solution is made up of a tetracycline compound present in Solution 15 containing the following components: 99.0 mmol/l NaCl; 24.0 mmol/l KCl; 0.8 mmol/l CaCl2; 0.6 mmol/l $MgCl_2$; 32 mmol/l $NaHCO_3$; 1.0 mmol/l $NaH_2PO_4$ at an osmolality (mOsm/kg) 302.

The pH of the ophthalmic preparation generally ranges from about 7.0 to 8.0, as measured by, for example, a Fisher pH Accumet Model 600. However, this pH range need not be rigidly adhered to, and it may be desirable to alter pH outside of this range, for instance, to improve ophthalmic drug penetration through the ocular surface. In view of the teachings provided herein, those skilled in the art may employ other pH ranges.

In preferred embodiments, the ophthalmic preparation is isotonic. However, the final osmolarity may be adjusted according to conditions present in the tear film or on the ocular surface (e.g., tear film osmolarity). For example, treatment of hypertonic tear films may make diluted preparations preferable. Conversely, preparations may be concentrated to hypertonic concentrations if therapeutically desirable. It is known that hypotonic and hypertonic eyedrops are brought rapidly to isotonicity by movement of water across the eye surface (Maurice et al. (1971) Exp. Eye Res. 11:30). Thus, when treating elevated tear film osmolarity (as associated, for example, with dry eye disorders), it may be preferable to dilute the ophthalmic preparation to hypotonicity while maintaining the proportions or balance of the electrolytes disclosed herein, and adjusting the concentration of the tetracycline compound such that the appropriate concentration is attained after entrance of water from the solution into the eye surface.

Ophthalmic preparations of the invention can be applied to the ocular surface by various methods known in the art. For example, the preparation can be topically to the ocular surface as eye drops. The preparation can also be applied using an eye cup so that the eye is bathed. The preparation can also be applied using a continuous or near continuous infusion device for ocular surface irrigation and/or wetting and/or drug delivery. The preparation may also be applied by devices that spray solutions as required onto the surface of the eye.

The invention shall be further described in the following working examples:

EXAMPLES

Animals

Male and female New Zealand white rabbits weighing between 2.5 and 3.5 kg were anesthetized with ketamine (100 mg/kg) and xylazine (10 mg/kg). Meibomian gland duct orifices were closed by cautery in the right eyes of all rabbits as previously described (7).

Treatment Groups

Four treatment groups (groups I, II, III, IV and V) were designated, each containing four rabbits: group I received no treatment; group II received tetracycline hydrochloride (Sigma Chemical, St. Louis, Mo.) intramuscularly at a dosage of 50 mg/kg/d (given as a solution of 500 mg/ml in sterile saline for injection USP) for five days each week; group III received tetracycline hydrochloride 1% in plastibase 50W and light mineral oil eyedrops (Achromycin, Lederle, Pearl River, N.Y.) four times a day for five days each week; and group IV received tetracycline hydrochloride 1% (Sigma Chemical, St. Louis, Mo.) in Solution 15-electrolyte vehicle (23) four times a day for five days each week. Solution 15 contains 99.0 mmol/l NaCl; 24.0 mmol/l KCl; 0.8 mmol/l CaCl2; 0.6 mmol/l $MgCl_2$; 32 mmol/l $NaHCO_3$; 1.0 mmol/l $NaH_2PO_4$ at an osmolality (mOsm/kg) of 302. Treatments began at 8 weeks post-op and continued until 20 weeks.

Treatment Evaluation

All rabbits were sacrificed at 20 weeks postoperatively by overdose with pentobarbital. At the time of death corneal epithelium was removed for measurement of corneal epithelial glycogen level as previously described (25). Conjunctival biopsies were then taken for counting of goblet cell density as previously described (10). Lower eyelids were then removed by sharp dissection and placed in one-half strength Karnovsky's fixative. The tissue was then dehydrated through graded alcohols and embedded in methacrylate. Three $\mu M$ sections were cut through the eyelids horizontally for light microscopy, and stained with alkaline giemsa.

Leukocytes were quantified in tissue sections using a method similar to that described by Sherwood et al. (26). For descriptive purposes, eyelid tissue was divided into three zones: 1) tarsal conjuntival epithelium, 2) underlying stroma, and 3) meibomian glands and adjacent tissue, including tarsal plate. Two separate sections, separated by a distance sufficient to provide two separate inflammatory cell populations, were examined for each eyelid. At a magnification of 40X, nine consecutive fields were counted for each zone in each section yielding a total of 18 fields per zone per eyelid. Leukocytes were identified as either neutrophils, eosinophils, basophils, or mastcells.

Quantification of corneal glycogen, conjunctival gobletcell density, and leukocytes was performed in a masked fashion. Corneal glycogen and conjunctival-goblet cell density was calculated as a percent of contralateral unoperated/untreated control eyes. Leukocytes were calculated as a mean per 40X field. Groups were compared using a pooled estimate of variance (Microstat, Microsoft Corporation).

Results

Figure 2:
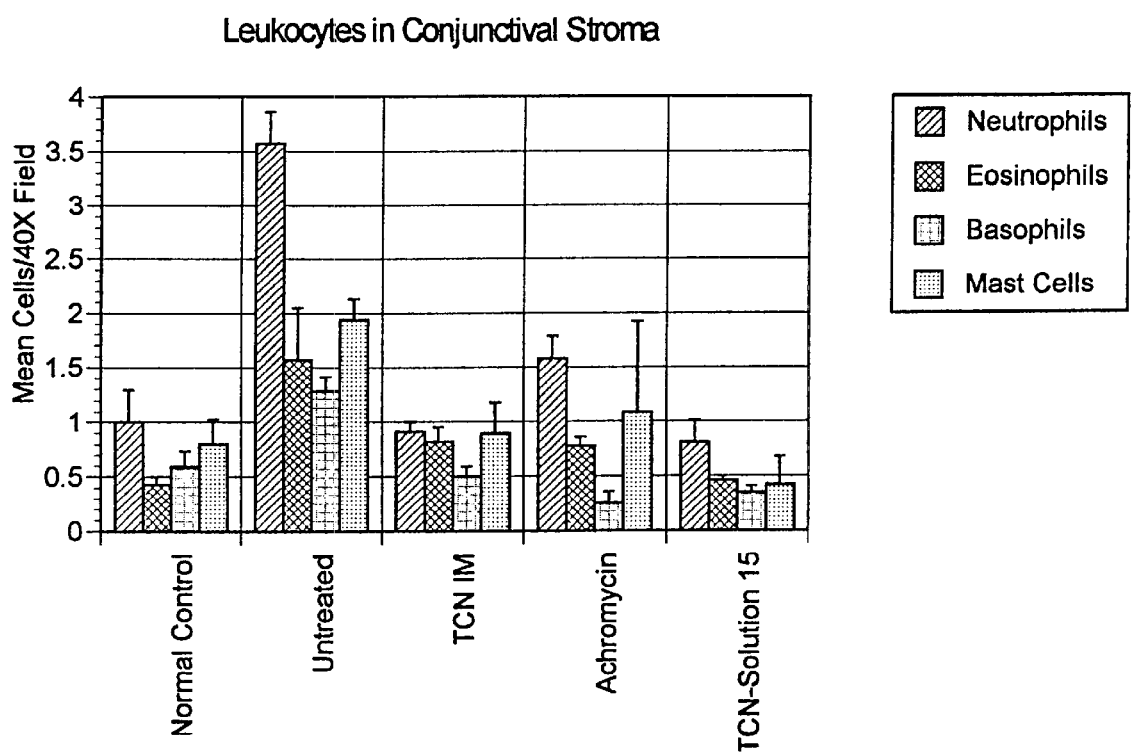
FIG. 2 is a graph showing leukocyte densities in conjunctival stroma of (a) normal control rabbits, (b) untreated control rabbits with meibomianitis/meibomian gland dysfunction, (c) rabbits treated with tetracycline in saline (administered intramuscularly (IM)), (d) rabbits treated with tetracycline in Achromycin™ light mineral oil eyedrops (administered topically), and (e) rabbits treated with tetracycline in Solution 15 (administered topically).
Figure 3:
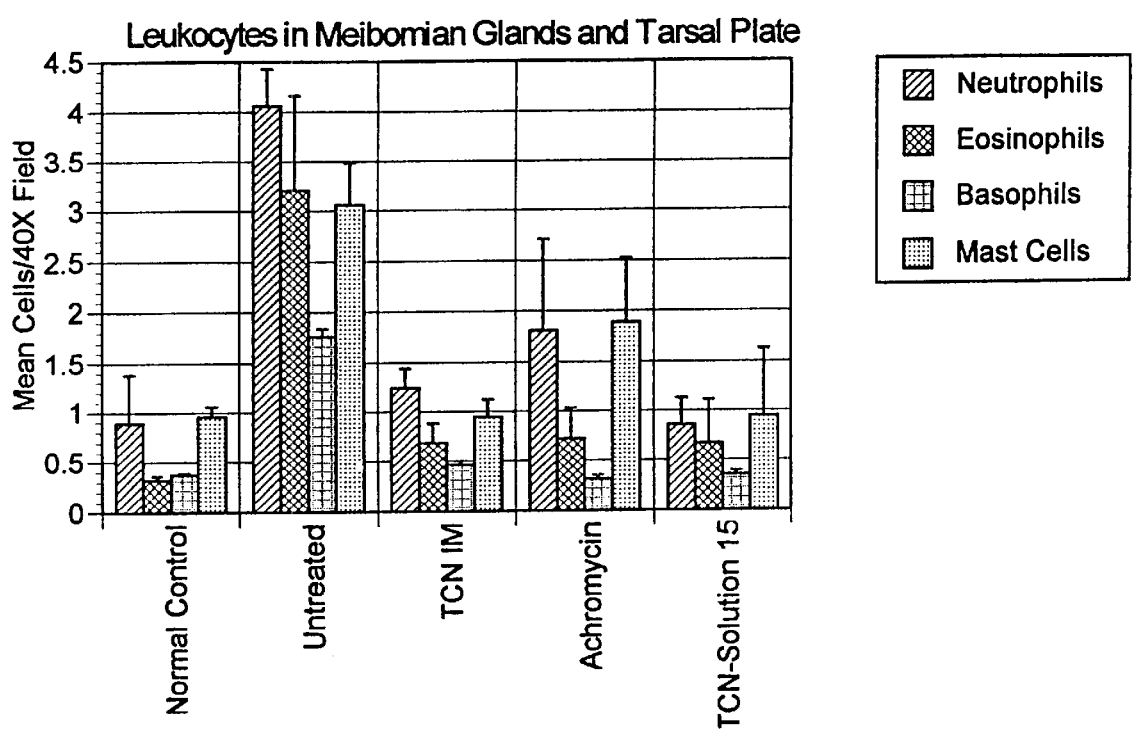
FIG. 3 is a graph showing leukocyte densities in meibomian glands and tarsal plate of (a) normal control rabbits, (b) untreated control rabbits with meibomianitis/meibomian gland dysfunction, (c) rabbits treated with tetracycline in saline (administered intramuscularly (IM)), (d) rabbits treated with tetracycline in Achromycin™ light mineral oil eyedrops (administered topically), and (e) rabbits treated with tetracycline in Solution 15 (administered topically).

Twenty weeks after meibomian gland orifice closure, untreated rabbits had a significant increase in eyelid tissue mast cells, eosinophils, neutrophils and basophils ($P<0.05$) relative to unoperated controls. Mast cells were not seen in the conjunctival epithelium of normal eyes nor after meibomian gland orifice closure. With this exception, all leukocyte types increased in all three tissue zones studied (FIGS. 1–3).

After 12 weeks of treatment, all rabbits treated with either systemic or topical tetracycline, in either vehicle, demonstrated a significant decrease in all leukocyte types in the conjunctival epithelium and meibomian gland/eye lid-zones ($P<0.05$). In the conjunctival stroma zone all rabbits treated with either systemic or topical tetracycline showed a significant decrease in mast cells, neutrophils, and basophils ($P<0.05$). Tetracycline in Solution 15 significantly decreased eosinophils in the stroma zone ($P<0.05$), whereas the decreases seen with the other tetracycline treatments did not attain statistical significance (FIGS. 1–3).

Figure 4:
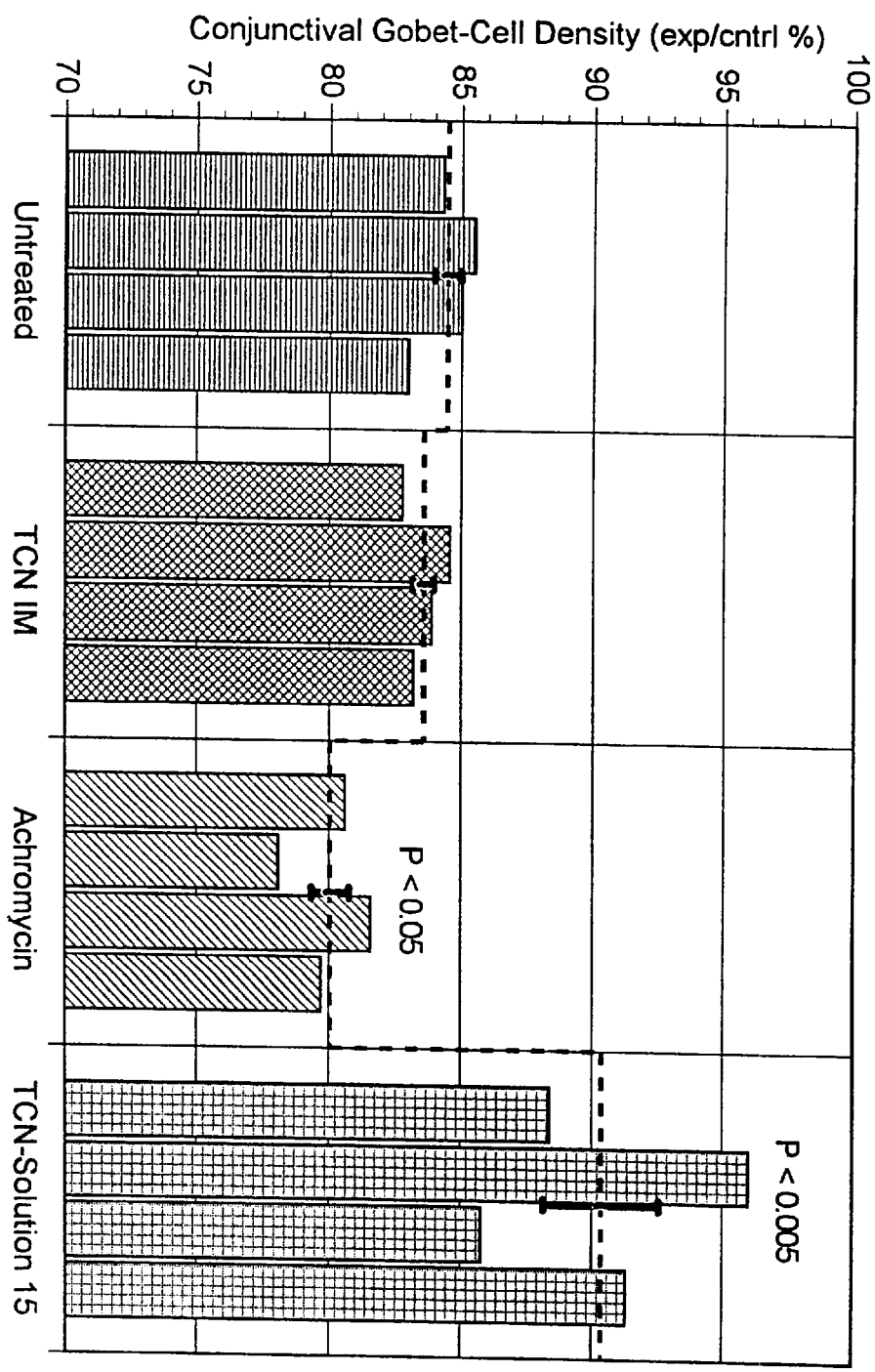
FIG. 4 is a graph showing the effect of the following tetracycline formulations on conjunctival goblet-cell density in a rabbit model for meibomianitis/meibomian gland dysfunction: (a) tetracycline in saline (administered intramuscularly (IM)), (b) tetracycline in Achromycin™ light mineral oil eyedrops (administered topically), and (c) tetracycline in Solution 15 (administered topically).

Goblet-cell density in rabbits 20 weeks after meibomian gland orifice closure had decreased to 84.5%±0.5 of contralateral normal controls (p<0.05). Treatment with systemic tetracycline had no effect on conjunctival goblet-cell density, while topical treatment with Achromycin significantly decreased goblet-cell density (80.1%±0.7, P<0.005). Topical treatment with tetracycline in Solution 15 significantly restored conjunctival goblet cells (90.4%±2.2, P<0.05) (FIG. 4).

Figure 5:
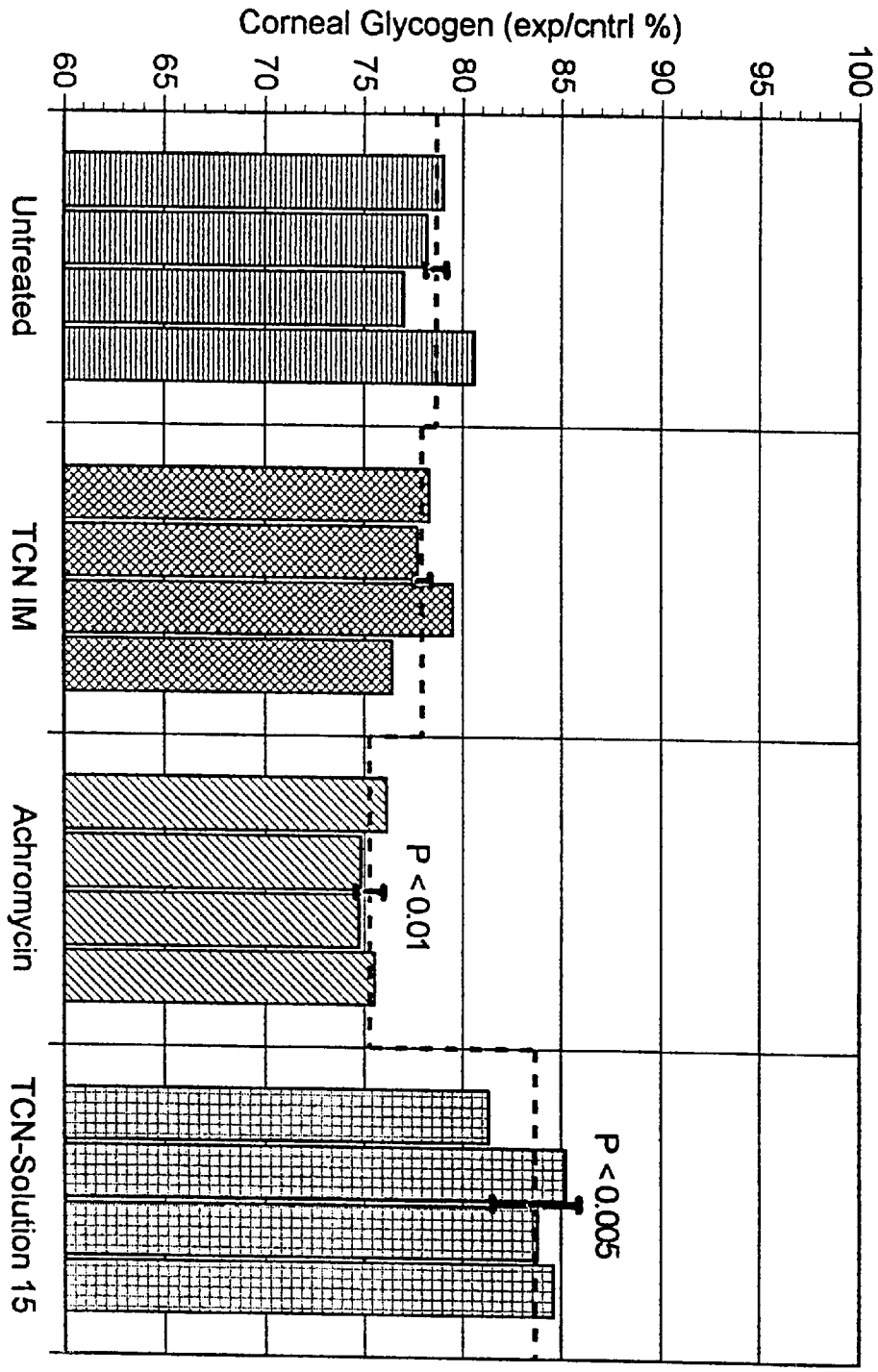
FIG. 5 is a graph showing the effect of the following tetracycline formulations on corneal glycogen in a rabbit model for meibomianitis/meibomian gland dysfunction: (a) tetracycline in saline (administered intramuscularly (IM)), (b) tetracycline in Achromycin™ light mineral oil eyedrops (administered topically), and (c) tetracycline in Solution 15 (administered topically).

Corneal epithelial glycogen in rabbits 20 weeks after meibomian gland orifice closure had decreased to 78.7%±0.8 of contralateral controls (p<0.05). Treatment with systemic tetracycline had no effect on corneal glycogen, while topical treatment with Achromycin significantly decreased corneal glycogen (75.3%±0.3, P<0.01). Topical treatment with tetracycline in Solution 15 significantly restored corneal glycogen (83.7%±0.9, P<0.005) (FIG. 5).

DISCUSSION

The present study demonstrates that systemic and topically administered tetracycline decreases the concentration of inflammatory cells in the eyelid and eye surface tissue of a rabbit model for meibomianitis and meibomian gland dysfunction. However, relatively low-dose topically applied tetracycline in the Solution 15 vehicle was more effective than relatively high-dose systemic tetracycline or topically applied Achromycin, and was the only treatment effective in restoring conjunctival goblet cells and corneal glycogen.

It has previously been shown that bacterial pathogens remain on the eyelids of patients successfully treated with tetracycline (2), that tetracycline does not affect the composition of meibomian gland secretions in meibomianitis (27), and that tetracycline levels are unlikely to be adequate to inhibit bacterial lipase activity (28). These data support the conclusion that the effectiveness of tetracycline in the treatment of meibomianitis is secondary to its ability to decrease inflammation.

The findings of the present studies also are consistent with those of Seedor et al. (29), who have demonstrated that systemically administered tetracycline decreases inflammatory cells in the corneal stroma of rabbits with corneal alkali bums.

A prominent feature of acne rosacea is the presence of inflammatory cells in the upper and middermis (30). The studies described herein suggest that the effectiveness of tetracycline in the treatment of acne rosacea dermatitis is due its ability to decrease tissue leukocytes. Topical steroids also decrease inflammation and have been used to treat meibomianitis. Unlike steroids, however, tetracyclines do not have the potential to increase intraocular pressure or to promote cataract formation.

Currently, tetracycline is generally administered systemically to patients to treat meibomianitis (5), or topically in oil-based preparations. While systemic tetracycline decreased tissue leukocytes in the current study, it did not improve conjunctival goblet-cell density or corneal glycogen. The topically administered commercial tetracycline tested in the current study significantly exacerbated the loss of goblet-cells and corneal glycogen seen with the dry-eye surface disease resulting from meibomian gland dysfunction. An ophthalmic preparation containing tetracycline in Solution 15, however, was able to decrease tissue leukocytes while simultaneously restoring conjunctival goblet-cell density and corneal glycogen in the currently disclosed rabbit model for meibomianitis and meibomian gland dysfunction. In addition, this ophthalmic preparation has the advantage of being a local rather than systemic therapy.

In conclusion, the results of the studies described herein suggest that topically applied ophthalmic preparations containing tetracycline in aqueous solution can be used clinically to treat meibomianitis and the dry eye surface disease resulting from meibomian gland dysfunction more effectively than either systemic tetracycline or commercial oil-based topical tetracycline. These ophthalmic preparations also may serve to treat other inflammatory ocular surface diseases and their complications.

EQUIVALENTS

Although the invention has been described with reference to its preferred embodiments, other embodiments can achieve the same results. Those skilled in the art will recognize or be able to ascertain using no more than routine experimentation, numerous equivalents to the specific embodiments described herein. Such equivalents are considered to be within the scope of this invention and are encompassed by the following claims.

INCORPORATION BY REFERENCE

All references and patents cited herein are hereby incorporated by reference in their entirety.

REFERENCES

1. Jenkins MS, Brown SI, Lempert SL, Weinberg RJ. Ocular rosacea. Am. J. Ophthalmol. 1979; 88:618–622.
2. Brown SI, Shahinian L. Diagnosis and treatment of ocular rosacea. Ophthalmol. 1978; 85:779–786.
3. Bartholomew B, Reid BJ, CHeesbrough MJ, MacDonald M, Galloway NR. Oxytetracycline in the treatment of ocular rosacea: a double-blind trial. Br. J. Ophthalmol. 1882; 66–386–388.
4. McCulley JP Blepharoconjunctivitis. Int. Ophthalmol Clin. 1984; 24:65–77.
5. McCulley JP, Dougherty JM. Blepharitis associated with acne rosacea and seborrheic dermatitis. Int Ophthalmol Clin. 1985;25:159–172.
6. Bowman RW, Miller KN, McCulley JP. Diagnosis and treatment of chronic blepharitis. In Wagner MD ed. Volume VII Module 10, Focal Points 1989: Clinical Modules for Ophthalmologists. San Francisco, American Academy of Ophthalmology, 1989.
7. Gilbard JP, Rossi SR, Gray Heyda K. Tear film and ocular surface changes after meibomian gland orificeclosure in the rabbit. Ophthalmology. 1989; 96:1180–1186.
8. Gutgesell VJ, Stem GA, Hood CI. Histopathology of meibomian gland dysfunction. Am J Ophthalmol. 1982; 94:383–387.
9. Robin JB, Jester JV, Nobe J, et al. In vivo transillumination biomicroscopy and photography of meibomian gland dysfunction: a clinical studya. Ophthalmology 1985; 92:1423–1426.
10. Gilbard, JP, Rossi SR, Gray KL. A new rabbit model for keratoconjuctivitis sicca. Invest Ophthalmol Vis Sci. 1987; 28:225–228.
11. Gilbard, JP, Rossi SR, Gray KL, Hanninen LA, Kenyon KR. Tear film osmolarity and ocular surface disease in two rabbit models for keratoconjunctivitis sicca. Invest Ophthalmol Vis Sci. 1988; 29:374–378.
12. Mathers WD. Ocular evaporation in meibomian gland dysfunction and dry eye. Ophthalmology. 1993; 100:347–351.
13. Hoeprich PD, Warshauer DM. Entry of tetracyclines into saliva and tears. Antimicrob Agents Chemother. 1974; 5:330–336.
14. Dilly PN, Mackie IA. Distribution of tetracycline in the conjunctiva of patients on long term systemic doses. Br J Ophthalmol. 1985; 69:25–28.
15. Golub LM, Lee HM, Lehrer G, Nemiroff A, McNamara TF, Kaplan R, Ramaurthy NS. Minocycline reduces gingival collagenolytic activity during diabetes. Preliminary observations and a proposed new mechanism of action. J Periodont Res. 1983; 18:516–526.
16. Golub LM, Ramamurthy N, McNamara TF, Gomes B, Wolff M, Casino A, Kapoor A, Zambon J, Ciancio S, Schneir M, Perry H. Tetracyclines inhibit tissue collagenase activity. A new mechanism in the treatment of periodontal disease. J Periodont Res. 1984; 19:651–655.
17. Golub LM, Wolff M, Lee HM, McNamara TF, Ramarnurthy NS, Zambon J, Cianci S. Further evidence that tetracyclines inhibit collagenase activity in human crevicular fluid and from other mammalian sources. J Periodont Res. 1985; 20:12–23.
18. Martin RR, Warr GA, Couch RB, Yeager H, Knight V. Effects of tetracycline on leukotaxis. J Infect Dis. 1974; 129:110–116.
19. Belsheim J, Gnarpe H, Persson S. Tetracyclines and host defense mechanisms: interference with leukocyte chemotaxis. Scand J Infect Dis. 1979; 11:141–145.
20. Esterly NB, Koransky JS, Furey NL, Trevisan M. Neutrophil chemotaxis in patients with acne receiving oral tetracycline therapy. Arch Dermatol. 1984; 120:1308–1313.
21. Elewski BE, Lamb BAJ, Sams WM, Gammon WR. In vivo suppression of neutrophil chemotaxis by systematically and topically administered tetracycline. J Am Acad Dermatol. 1983; 8:807–812.
22. Forsgren A, Schmneling D, Quie PG. Effect of tetracycline on the phagocytic function of human leukocytes. J Infect Dis. 1974; 130:412–415.
23. Gilbard JP, Rossi SR, Gray Heyda K. Ophthalmic solutions, the ocular surface, and a unique therapeutic artificial tear formulation. Am J Ophthalmol. 1989; 107:348–355.
24. Gilbard JP, Rossi SR. An electrolyte-based solution that increases corneal glycogen and conjunctival goblet cell density in a rabbit model for keratoconjunctivitis sicca. Ophthalmology. 1992; 99:600–604.
25. Friend J, Kiorpes T, Kinoshita S. Glycogen and DNA content of corneal epithelium: Comparison of preparation methods. Invest Ophthalmol Vis Sci. 1983; 24:203–207.
26. Sherwood MB, Grierson I, Millar L, Hitchings RA. Long-term morphologic effects of antiglaucoma drugs on the conjunctiva and tenon's capsule in glaucomaatous patients. Ophthalmology. 1989; 96:327–335.
27. Nicolaides N, Santos EC, Smith RE: Meibum lipids in rosacea, blepharitis, and chalazia. Inves Ophthalmol Vis Sci 1983: 24(suppl): 78.
28. Salamon SM. Tetracyclines in ophthalmology. Surv Ophthalmol. 1985; 29:265–275.

29. Seedor JA, Perry HD, McNamara TF, Golub LM, Buxton DF, Guthrie DS. Systemic tetracycline treatment of alkali-induced corneal ulceration in rabbits. Arch Ophthalmol. 1987; 105:268–271.
30. Marks R, Harcourt-Webster JN. Histopathology of rosacea. Arch. Derm. 1969; 100:683–691.

What is claimed is:

1. An ophthalmic preparation for topical application to the eye, the preparation comprising an aqueous solution containing (a) a tetracycline compound in an amount sufficient to treat an ocular disease characterized by eye surface inflammation; and (b) a balance of electrolytes selected from the group consisting of potassium, chloride, bicarbonate and sodium, wherein said potassium is present at a concentration of about 22.0 to 43.0 mM/l, said bicarbonate is present at a concentration of about 29.0 to 50.0 mM/l, said sodium is present at a concentration of about 130.0 to 140.0 mM/l, and said chloride is present at a concentration of about 118.0 to 136.5 mM/l, or a therapeutically effective dilution or concentration of said solution.

2. The ophthalmic preparation of claim 1 wherein said solution has an osmolarity of about 296–325 mOsm/Kg.

3. The ophthalmic preparation of claim 1, wherein said solution further comprises a balance of electrolytes selected from the group consisting of calcium, magnesium and phosphate, wherein said calcium is present at a concentration of about 0.5 to 2.0 mM/l, said magnesium is present at a concentration of about 0.3 to 1.1 mM/l, and said phosphate is present at a concentration of about 0.8 to 2.2 mM/l.

4. The ophthalmic preparation of claim 3 wherein said solution has an osmolarity of about 296–325 mOsm/Kg.

5. The ophthalmic preparation of claim 1 wherein said tetracycline compound is tetracycline hydrochloride.

6. The ophthalmic preparation of claim 1 wherein said tetracycline compound is tetracycline hydrochloride present at a concentration of about 0.125% to 2% when the solution is isotonic or attains isotonicity.

7. An aqueous ophthalmic solution comprising:
(a) a tetracycline compound at a concentration equivalent in anti-inflammatory potency to tetracycline at a concentration of about 0.125% to 2% when the solution is isotonic or attains isotonicity;
(b) potassium at a concentration of about 22.0 to 43.0 mM/l;
(c) bicarbonate at a concentration of about 29.0 to 50.0 mM/l;
(d) sodium at a concentration of about 130.0 to 140.0 mM/l, and
(e) chloride at a concentration of about 118.0 to 136.5 mM/l, or a therapeutically effective dilution or concentration of said solution.

8. The ophthalmic solution of claim 7 wherein said solution has an osmolarity of about 296–325 mOsm/Kg.

9. The ophthalmic solution of claim 7 further comprising:
(a) calcium at a concentration of about 0.5 to 2.0 mM/l,
(b) magnesium at a concentration of about 0.3 to 1.1 mM/l, and
(c) phosphate at a concentration of about 0.8 to 2.2 mM/l.

10. The ophthalmic solution of claim 9 wherein said solution has an osmolarity of about 296–325 mOsm/Kg.

11. A method of treating eye surface inflammation or dryness comprising topically applying to the surface of an eye of a subject suffering from said disorder an aqueous ophthalmic solution comprising: (a) a tetracycline compound in an amount sufficient to treat an ocular disease characterized by eye surface inflammation; and (b) a balance of electrolytes selected from the group consisting of potassium, chloride, bicarbonate and sodium, wherein said potassium is present at a concentration of about 22.0 to 43.0 mM/l, said bicarbonate is present at a concentration of about 29.0 to 50.0 mM/l, said sodium is present at a concentration of about 130.0 to 140.0 mM/l, and said chloride is present at a concentration of about 118.0 to 136.5 mM/l, or a therapeutically effective dilution of said solution.

12. The method of claim 11 wherein said solution has an osmolarity of about 296–325 mOsm/Kg.

13. The method of claim 11 wherein said tetracycline compound is tetracycline hydrochloride at a concentration of about 0.123% to 2% when the solution is isotonic or attains isotonicity.

14. A method of simultaneously reducing inflammation and dryness of an ocular surface, comprising topically applying to said ocular surface an aqueous ophthalmic solution comprising: (a) a tetracycline compound in an amount sufficient to treat an ocular disease characterized by eye surface inflammation; and (b) a balance of electrolytes selected from the group consisting of potassium, chloride, bicarbonate and sodium, wherein said potassium is present at a concentration of about 22.0 to 43.0 mM/l, said bicarbonate is present at a concentration of about 29.0 to 50.0 mM/l, said sodium is present at a concentration of about 130.0 to 140.0 mM/l, and said chloride is present at a concentration of about 118.0 to 136.5 mM/l, or a therapeutically effective dilution of said solution.

15. An ophthalmic preparation comprising an aqueous solution containing one or more tetracycline compounds in an amount sufficient to treat an ocular disease characterized by eye surface inflammation.

16. The ophthalmic preparation of claim 15 wherein said tetracycline compound is tetracycline hydrochloride.

17. The ophthalmic preparation of claim 16 wherein said tetracycline hydrochloride is present at a concentration of about 0.125% to 2% when the solution is isotonic or attains isotonicity.

* * * * *